United States Patent [19]

Irmscher et al.

[11] Patent Number: 4,654,350
[45] Date of Patent: Mar. 31, 1987

[54] GABA-AGONISTIC IMIDAZO(4,5-C)PYRIDINES USEFUL AS PHARMACEUTICALS

[75] Inventors: Klaus Irmscher; Otto Saiko, both of Darmstadt; Klaus-Otto Minck, Ober-Ramstadt; Hans-Peter Wolf, Alsbach, all of Fed. Rep. of Germany

[73] Assignee: Merck Patent Gesellschaft Mit Beschrankter Haftung, Darmstadt, Fed. Rep. of Germany

[21] Appl. No.: 873,560

[22] Filed: Jun. 12, 1986

Related U.S. Application Data

[63] Continuation-in-part of Ser. No. 746,706, Jun. 20, 1985, abandoned, which is a continuation-in-part of Ser. No. 451,378, Dec. 20, 1982, abandoned.

[30] Foreign Application Priority Data

Dec. 19, 1981 [DE] Fed. Rep. of Germany ....... 3150486

[51] Int. Cl.$^4$ ..................... A61K 31/44; C07D 471/04
[52] U.S. Cl. .................................. 514/303; 546/118
[58] Field of Search ......................... 546/118; 514/303

[56] References Cited

U.S. PATENT DOCUMENTS 4,347,315  8/1982  Krenitsky et al. .................... 435/87

Primary Examiner—Henry R. Jiles
Assistant Examiner—Bernard I. Dentz
Attorney, Agent, or Firm—Millen & White

[57] ABSTRACT

Imidazo(4,5-c)pyridines of the formula

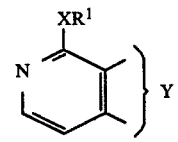

wherein
X is O, S or NH;
Y is $-NR^2-CH=N-$ or $-N=CH-NR^2-$;
$R^1$ is 1-benzothienylmethyl, naphthylmethyl, or benzyl which is mono- or di-substituted by F, Cl, $NO_2$, $CF_3$ or a combination thereof, and;
$R^2$ is alkyl of 1–4 C atoms or cyclopropylmethyl,
or a physiologically acceptable acid addition salt thereof,
have valuable pharmacological activity, e.g., as GABA agonists.

23 Claims, No Drawings

GABA-AGONISTIC IMIDAZO(4,5-C)PYRIDINES USEFUL AS PHARMACEUTICALS

This application is a continuation-in-part of Ser. No. 746,706 filed 6,20,85 which, in turn, is a continuation-in-part of Ser. No. 451,378 filed 12,20,82 which are abandoned.

This invention relates to new pharmacologically active compounds.

SUMMARY OF THE INVENTION

It is an object of this invention to provide new compounds having valuable properties, in particular compounds which can be used for the preparation of medicaments.

Upon further study of the specification and appended claims, further objects and advantages of this invention will become apparent to those skilled in the art.

These objects have been achieved by providing new imidazo(4,5-c)-pyridines of Formula I

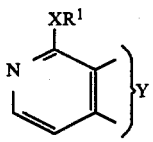

wherein
X is O, S or NH;
Y is $-NR^2-CH=N-$ or $-N=CH-NR^2-$;
$R^1$ is 1-benzothienylmethyl, naphthylmethyl, or benzyl which is mono- or di-substituted by F, Cl, $NO_2$ and/or $CF_3$; and
$R^2$ is alkyl of 1–4 C atoms or cyclopropylmethyl; and physiologically acceptable acid addition salts thereof.

Formula I includes the 1H-imidazo(4,5-c)-pyridines of Formula Ia (=Formula I with $Y=-N=CH-NR^2-$; compare "The Ring-index", 2nd edition, American Chemical Society, 1960, No. 1194) and the 3H-imidazo(4,5-c)-pyridines of Formula Ib (=Formula I with $Y=-NR^2-CH=N-$; compare "The Ring-index", loc. cit., No. 1195).

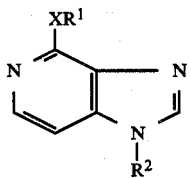

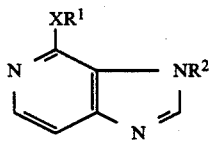

Of these compounds, those of Formula Ib are preferred.

It has been found that these compounds have valuable pharmacological properties, coupled with good tolerance. In particular, they have selectively GABA-agonistic actions (e.g., as measured by the inhibition of bicucullin-induced spasms, for example by the method of D. R. Curtis et al., Brain Res., Volume 33 (1971), pages 57 et seq, and M. Perez de la Mora, Biochem. Pharmacology, Volume 22 (1973), pages 2635 et seq) and/or benzodiazepine-antagonistic actions. In vitro, the substances exhibit powerful bonding to benzodiazepine receptors (detectable, for example, by the method of R. F. Squires and C. Braestrup, Nature (London), Volume 266 (1977), pages 732–734, and H. Möhler and T. Okada, Life Sciences, Volume 20 (1977), pages 2101–2110; Science (Washington, D.C.), Volume 198 (1977), pages 849–851). Furthermore, anorectic activities can be shown (e.g., according to the method of Levine and Morley, Science (Washington, D.C.), Volume 217 (1982), page 77 All of the disclosures are incorporated by reference herein.

The compounds also exhibit an anticonvulsive action. Specifically, 4-o-chlorobenzyloxy-1-methyl-1H-imidazo(4,5-c)pyridine has been shown to be a potent anticonvulsant.

In detail, the anticonvulsive action can be established by various tests cited by R. J. Porter et al. in Cleveland Clinic Quarterly, Volume 51 (1984), pages 294–305, and the references cited therein.

Furthermore, the anticonvulsive action can be demonstrated, for example, against convulsive and lethal doses of caffeine, bicuculline, picrotoxin, strychnine or pentetrazole to mice and rats, f.e. according to the method of Orloff et al., Proc. Soc. Exptl. Biol. Med., Volume 70 (1949), pages 254 ff.

All of these disclosures are incorporated by reference herein too.

The compounds can therefore be used as active agents in medicaments in human and veterinary medicine, e.g., for administration to mammals, including humans. They can also be used as intermediate products for the preparation of other active compounds in medicaments.

DETAILED DISCUSSION

In the compounds of Formula I, X is preferably O or S.

The radical $R^1$ is preferably 1-benzothienyl-3-methyl, o-, m- or p-fluorobenzyl, o-, m- or p-chlorobenzyl, o-, m- or p-nitrobenzyl, o-, m- or p-trifluoromethylbenzyl, or 2,3-, 2,4-, 2,5-, 2,6-, 3,4- or 3,5-dichlorobenzyl; furthermore included, for example, are 1-benzothienyl-2-methyl, naphthyl-1- or -2-methyl, 2,3-, 2,4-, 2,5-, 2,6-, 3,4- or 3,5-difluorobenzyl, 2,3-, 2,4-, 2,5-, 2,6-, 3,4- or 3,5-dinitrobenzyl, 2,3-, 2,4- 2,5-, 2,6-, 3,4- or 3,5-bis(trifluoromethyl)-benzyl, 2-chloro-3-, -4-, -5- or -6-fluorobenzyl, 3-chloro-2-, -4-, -5-, or -6-fluorobenzyl, 4-chloro-2- or -3-fluorobenzyl, 2-fluoro-3-, -4-, -5- or -6-nitrobenzyl, 3-fluoro-2-, -4-, -5- or -6-nitrobenzyl, 4-fluoro-2- or -3-nitrobenzyl, 2-fluoro-3-, -4-, -5- or -6-trifluoromethylbenzyl, 3-fluoro-2-, -4-, -5- or -6-trifluoromethylbenzyl, 4-fluoro-2- or -3-trifluoromethylbenzyl, 2-chloro-3-, -4-, -5- or -6-nitrobenzyl, 3-chloro-2-, -4-, -5- or -6-nitrobenzyl, 4-chloro-2- or -3-nitrobenzyl, 2-chloro-3-, -4-, -5- or -6-trifluoromethylbenzyl, 3-chloro-2-, -4-, -5: or -6-trifluoromethylbenzyl, 4-chloro-2- or -3-trifluoromethylbenzyl, 2-nitro-3-, -4-, -5- or -6-trifluoromethylbenzyl, 3-nitro-2-, -4-, -5- or -6-trifluoromethylbenzyl, or 4-nitro-2- or -3-trifluoromethylbenzyl.

The radical $R^2$ is preferably methyl, or ethyl or cyclopropylmethyl; or also propyl, isopropyl, butyl, isobutyl, sec-butyl or tert-butyl.

The present invention particularly relates to those compounds of Formula I in which at least one of the radicals mentioned has one of the above mentioned preferred meanings. Some preferred groups of compounds can be defined by the following partial Formulae Ic to Ie, which correspond to the Formulae I, or Ia or Ib, but in which in Ic X is O;
in Id X is S;
in Ie X is NH.

Further preferred groups of compounds are those of the partial Formulae If to Ih, which correspond to the Formulae I or Ia to Ie, but in which in If $R^1$ is 1-benzothienylmethyl, fluorobenzyl, chlorobenzyl, trifluoromethylbenzyl, dichlorobenzyl or chlorofluorobenzyl;

in Ig $R^1$ is 1-benzothienyl-3-methyl, o-fluorobenzyl, o-chlorobenzyl, o-trifluoromethylbenzyl, 2,4- or 2,6-dichlorobenzyl or 2-chloro-6-fluorobenzyl;

in Ih $R^1$ is 1-benzothienyl-3-methyl;

in Ii $R^1$ is 1-benzothienyl-3-methyl and $R^2$ is methyl.

This invention furthermore relates to a process for the preparation of compounds of Formula I and of their physiologically acceptable salts, comprising, reacting a compound of Formula II

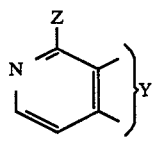

II wherein
Z is F, Cl, Br, I, OH, SH, $SR^3$, $SOR^3$, $SO_2R^3$ or $NH_2$,
$R^3$ is alkyl of 1–4 C atoms, phenyl or benzyl and
Y is as defined above, or one of its reactive derivatives, with a compound of Formula III

 HX—$R^1$    III wherein
X and $R^1$ are as defined above, or one of its reactive derivatives, or reacting a compound of Formula IV

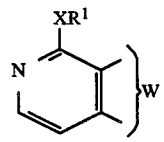

IV wherein
W is —NH—CH=N— or —N=CH—NH—,
with a compound of Formula V

 Z—$R^2$    V wherein
$R^2$ and Z are as defined above, or one of its reactive derivatives,
or reacting a compound of Formula VI

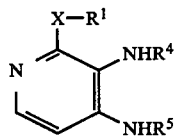

VI wherein
one of the radicals $R^4$ or $R^5$ is H and the other is $R^2$, and
X and $R^1$ are as defined above,
with formic acid or one of its reactive derivatives,
and/or, if appropriate, converting a compound of Formula I into one of its physiologically acceptable acid addition salts by treatment with an acid.

The compounds of Formula I moreover can be prepared by methods which are known per se, such as described in the literature (for example in the standard works, such as Houben-Weyl, Methoden der Organischen Chemie [Methods of Organic Chemistry], Georg-Thieme-Verlag, Stuttgart), and in particular under reaction conditions which are known and suitable for the reactions mentioned. Variants which are known per se and are not mentioned here in more detail can also be used.

If desired, the starting materials can also be formed in situ, in a manner such that they are not isolated from the reaction mixture but are immediately reacted further to give the compounds of Formula I. On the other hand, it is possible to carry out the reaction in stages, in which case further intermediate products can be isolated The compounds of Formula I are preferably obtained by reacting imidazo(4,5-c)pyridines of Formula II or their reactive derivatives (for example the corresponding metal alcoholates or metal mercaptides) with compounds of Formula III or their reactive derivatives (for example the corresponding metal alcoholates, metal mercaptides or reactive esters, in particular the corresponding chlorides or bromides of the formula $R^1Cl$ or $R^1Br$).

Some of the starting substances of the Formulae II and III are known. Those which are not known can be prepared by fully conventional methods which are known per se. Thus, the IH-imidazo(4,5-c)pyridines of Formula II can be obtained, for example, by condensation of 2-Z-3-amino-4-$NHR^2$-pyridines with formic acid/acetic anhydride, and the 3H-imidazo(4,5-c)pyridines of Formula II can be obtained by condensation of 2-Z-3-$ZHR^2$-4-aminopyridines with formic acid/acetic anhydride. In the compounds of Formula II, the radical Z is preferably a chlorine atom. The starting materials used in these preparative reactions for the compounds of Formula II or III are also either known or prepared by fully conventional methods from readily available starting materials.

In detail, the reaction of II with III can be carried out in the presence or absence of an inert solvent at temperatures of about −20° to 250°, preferably 60° to 150°. Examples of suitable solvents include hydrocarbons, such as benzene, toluene, xylenes or mesitylene; tertiary bases, such as triethylamine; pyridine or picolines; alcohols, such as methanol, ethanol or butanol; glycols and glycol ethers, such as ethylene glycol, diethylene glycol or 2-methoxy-ethanol; ketones, such as acetone; ethers, such as tetrahydrofuran or dioxane; amides, such as dimethylformamide; and sulfoxides, such as dimethylsulfoxide. Mixtures of these solvents are also suitable.

Alcohols and mercaptans of Formula III (X=O or S) are preferably first converted into the corresponding sodium or potassium alcoholates or mercaptides by reaction with sodium, potassium, sodium or potassium ethylate or sodium or potassium hydride.

The amines of Formula III (X=NH) are particularly suitable for reaction without a solvent, in the melt. Their reaction with compounds of Formula II (Z=Cl) is effected, for example, by heating to about 160°-190° for several hours; an excess of amine is advantageously used.

The compounds of Formula I can furthermore be obtained by N-alkylation of the imidazo(4,5-c)pyridines of Formula IV with compounds of Formula V or their reactive derivatives. The starting substances of Formula IV are new, but can be obtained fully conventionally in a manner which is known per se, for example by reaction of 2-Z-3,4-diamino-pyridines with formic acid/acetic anhydride to give 2-Z-imidazo(4,5-c)pyridines and subsequent reaction with compounds of Formula III, by the methods described above. These two reaction steps can also be changed, the synthesis then passing through the corresponding 2-XR$^1$-3,4-diaminopyridines. Starting materials required for preparation of the compounds of Formula IV are either known or preparable from readily available starting materials using fully conventional methods.

Suitable compounds of Formula V are, above all, the corresponding chlorides, bromides and iodides, for example methyl chloride, bromide or iodide, ethyl chloride, bromide or iodide or cyclopropylmethyl chloride, bromide or iodide, and also other reactive esters of alcohols of the formula R$^2$—OH, for example methyl p-toluenesulfonate or dimethyl sulfate. The N-alkylation is effected, for example, in the presence of one of the above mentioned solvents (for example ethanol or acetone) at temperatures of about 0° to 100°. It is preferable to add a base, such as potassium carbonate.

The compounds of Formula I can also be obtained by reacting diaminopyridines of Formula VI (which can be prepared, for example, by reaction of known or readily preparable (from starting materials) 2-Z-3-NHR$^4$-4-NHR$^5$-pyridines with a compound of Formula III under the above mentioned conditions) with formic acid or one of its reactive derivatives, for example s-triazine or a trialkyl orthoformate, in which the alkyl group preferably has 1-4 C atoms. The reaction preferably proceeds in the presence or absence of one of the inert solvents mentioned, at temperatures of about 20° to about 200°. It may be advantageous to add a condensing agent, such as acetic anhydride. In the case of s-triazine, the reaction is preferably carried out without a solvent, for example under the conditions mentioned in U.S. Patent Specification No. 2,841,585.

A base of Formula I can be conventionally converted into the corresponding acid addition salt with an acid. Suitable acids for this reaction are those which give physiologically acceptable salts. Thus, it is possible to use inorganic acids, for example sulfuric acid, nitric acid, hydrogen halide acids, such as hydrochloric acid or hydrobromic acid, phosphoric acids, such as orthophosphoric acid, or sulfamic acid, as well as organic acids, in particular aliphtic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono- and -disulfonic acids and laurylsulfuric acid.

The present invention furthermore relates to the use of the compounds of Formula I and their physiologically acceptable salts for the preparation of pharmaceutical formulations, in particular by a non-chemical route. For this, they can be brought into a suitable dosage form, together with at least one solid, liquid and/or semi-solid excipient or auxiliary, and if appropriate in combination with one or more other active compound(s).

The invention also relates to agents, in particular pharmaceutical formulations, containing at least one compound of Formula I and/or one of its physiologically acceptable salts.

These formulations can be used as medicaments in human or veterinary medicine. Suitable excipients are organic or inorganic substances which are suitable for enteral (for example oral) or parenteral administration or topical application and with which the new compounds do not react, for example water, vegetable oils, benzyl alcohols, polyethylene glycols, glycerol triacetate, gelatine, carbohydrates, such as lactose or starch, magnesium stearate, talc or vaseline. Tablets, dragees, capsules, syrups, elixirs or drops, in particular, are used for oral administration, suppositories are used for rectal administration, solutions, preferably oily or aqueous solutions, and suspensions, emulsions or implants are used for enteral administration, and ointments, creams or powders are used for topical application.

The new compounds can also be lyophilized and the resulting lyophilizates can be used, for example, for the preparation of injection products. The formulations mentioned can be sterilized and/or may contain auxiliaries, such as lubricants, preservatives, stabilizers, wetting agents, emulsifiers, salts for influencing the osmotic pressure, buffer substances, colorants, flavoring agents and/or aroma adding substances. If desired, they can also contain one or more other active compounds, for example one or more vitamins.

The invention furthermore relates to the use of the compounds of Formula I in combating illnesses, in particular illness conditions which can be influenced using GABA-agonists, for example cerebral infarction, epilepsy, delayed dyskinesia, Huntington's chorea, abstinence syndrome in alcoholics, alcohol withdrawal spasms, spastic conditions, anxiety, sleep disorders or pain, generally in the prophylaxis of cell decay caused by spasms or alcohol, also for influencing physiological tiredness, and furthermore for antagonizing the sedating, muscle-relaxing, atactic, hypotensive and respiration-depressive properties of tranquilizing benzodiazepines, in particular 1,4- and 1,5-benzodiazepines, and for antagonizing non-benzodiazepines if they agonistically attack the benzodiazepine receptor, in particular for antagonizing the sedative action of other medicaments, for example as an antidote for intoxication conditions in which excessive intake of benzodiazepines participates, e.g., in overdoses, or for shortening anesthesia induced by benzodiazepines, and to their use in the therapeutic treatment of the human or animal body.

The substances of this invention are as a rule administered analogously to known active substances, such as phenytoin or progabid, preferbly in dosages of about 1 to 500 mg, in particular 5 to 100 mg per dosage unit. The daily dosage is preferably about 0.02 to 10 mg/kg of body weight. However, the specific dose for each particular patient depends on the usual most diverse factors, for example on the effectiveness of the particular compounds used, on the age, body weight, general state of health, sex, and diet of the patient, on the administration time and route, and on the excretion rate, medicament combination and severity of the particular illness to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius; unless otherwise indicated, all parts and percentages are by weight.

In the examples which follow, "customary working up" means:

If necessary, water or dilute sodium hydroxide solution is added. The mixture is extracted with an organic solvent, such as ethyl acetate, chloroform or methylene chloride. The phases are separated. The organic phase is dried over sodium sulfate, filtered and evaporated and the residue is purified by chromatography and/or crystallization.

EXAMPLE 1

15.84 g of 1-benzothienyl-3-methanol is dissolved in 110 ml of dimethylformamide; 2.88 g of NaH is added and the mixture is stirred at 20° for 1 hour. After a solution of 16.76 g of 4-chloro-1-methyl-1H-imidazo(4,5-c)pyridine [m.p. 132°–134°; obtainable by reaction of 4-methylamino-3-nitropyridine with HCl/SnCl$_2$ to give 3-amino-2-chloro-4-methylaminopyridine (m.p. 170°–173°) and reaction with HCOOH/acetic anhydride] in 70 ml of dimethylformamide has been added, the mixture is stirred at 90°–95° for 15 hours. The mixture is evaporated and the residue is worked up in the customary manner to give 4-(1-benzothienyl-3-methoxy)-1-methyl-1H-imidazo(4,5-c)pyridine of m.p. 200°–204° (from ethyl acetate/tetrahydofuran).

EXAMPLE 2

4-(1-Benzothienyl-3-methoxy)-3-methyl-3H-imidazo(4,5-c)pyridine of m.p. 160°–162° is obtained analogously to Example 1 from 1-benzothienyl-3-methanol and 4-chloro-3-methyl-3H-imidazo(4,5-c)pyridine [m.p. 160°–161°; obtainable by reaction of 4-amino-2-chloro-3-p-toluenesulfono-amidopyridine with dimethylsulfate/K$_2$CO$_3$ in acetone to give 4-amino-2-chloro-3-methylamino-pyridine (m.p. 62°–65°) and reaction with HCOOH/acetic anhydride].

EXAMPLES 3 TO 62

The following compounds are obtained analogously to Example 1 from the corresponding 4-chloro-imidazo(4,5-c)pyridines with the corresponding alcohols:

3. 4-(1-Benzothienyl-2-methoxy)-1-methyl-1H-imidazo(4,5-c)pyridine of m.p. 156°–158°.
4. 4-(Naphthyl-1-methoxy)-1-methyl-1H-imidazo(4,5-c)pyridine of m.p. 199°–200°.
5. 4-(Naphthyl-2-methoxy)-1-methyl-1H-imidazo(4,5-c)pyridine of m.p 109°–110°.
6. 4-o-Fluorobenzyloxy-1-methyl-1H-imidazo(4,5-c)pyridine of m.p. 108°–110°.
7. 4-m-Fluorobenzyloxy-1-methyl-1H-imidazo(4,5-c)pyridine.
8. 4-p-Fluorobenzyloxy-1-methyl-1H-imidazo(4,5-c)pyridine.
9. 4-o-Chlorobenzyloxy-1-methyl-1H-imidazo(4,5-c)pyridine of m.p. 132°–135°.
10. 4-m-Chlorobenzyloxy-1-methyl-1H-imidazo(4,5-c)pyridine.
11. 4-p-Chlorobenzyloxy-1-methyl-1H-imidazo(4,5-c)pyridine of m.p. 142°–146°.
12. 1-Methyl-4-o-nitrobenzyloxy-1-methyl-1H-imidazo(4,5-c)pyridine.
13. 1-Methyl-4-m-nitrobenzyloxy-1-methyl-1H-imidazo(4,5-c)pyridine.
14. 1-Methyl-4-p-nitrobenzyloxy-1-methyl-1H-imidazo(4,5-c)pyridine.
15. 1-Methyl-4-o-trifluoromethylbenzyloxy-1-methyl-1H-imidazo(4,5-c)pyridine of m.p. 108°–110°.
16. 1-Methyl-4-m-trifluoromethylbenzyloxy-1-methyl-1H-imidazo(4,5-c)pyridine.
17. 1-Methyl-4-p-trifluoromethylbenzyloxy-1-methyl-1H-imidazo(4,5-c)pyridine.
18. 4-(2,3-Dichlorobenzyloxy)-1-methyl-1H-imidazo(4,5-c)pyridine.
19. 4-(2,4-Dichlorobenzyloxy)-1-methyl-1H-imidazo(4,5-c)pyridine of m.p. 130°–132°.
20. 4-(2,5-Dichlorobenzyloxy)-1-methyl-1H-imidazo(4,5-c)pyridine.
21. 4-(2,6-Dichlorobenzyloxy)-1-methyl-1H-imidazo(4,5-c)pyridine.
22. 4-(3,4-Dichlorobenzyloxy)-1-methyl-1H-imidazo(4,5-c)pyridine.
23. 4-(3,5-Dichlorobenzyloxy)-1-methyl-1H-imidazo(4,5-c)pyridine.
24. 4-(2,4-Dinitrobenzyloxy)-1-methyl-1H-imidazo(4,5-c)pyridine.
25. 4-(3,4-Dinitrobenzyloxy)-1-methyl-1H-imidazo(4,5-c)pyridine.
26. 4-(3,5-Dinitrobenzyloxy)-1-methyl-1H-imidazo(4,5-c)pyridine.
27. 4-(2-Chloro-6-fluorobenzyloxy)-1-methyl-1H-imidazo(4,5-c)pyridine.
28. 4-(2-Chloro-4-nitrobenzyloxy)-1-methyl-1H-imidazo(4,5-c)pyridine.
29. 4-(2-Chloro-5-nitrobenzyloxy)-1-methyl-1H-imidazo(4,5-c)pyridine.
30. 4-(4-Chloro-2-nitrobenzyloxy)-1-methyl-1H-imidazo(4,5-c)pyridine.
31. 4-(4-Chloro-3-nitrobenzyloxy)-1-methyl-1H-imidazo(4,5-c)pyridine.
32. 4-(5-Chloro-2-nitrobenzyloxy)-1-methyl-1H-imidazo(4,5-c)pyridine.
33. 4-(1-Benzothienyl-2-methoxy)-3-methyl-3H-imidazo(4,5-c)pyridine.
34. 4-(Naphthyl-1-methoxy)-3-methyl-3H-imidazo(4,5-c)pyridine of m.p. 141°–142°.
35. 4-(Naphthyl-2-methoxy)-3-methyl-3H-imidazo(4,5-c)pyridine of m.p. 171°.
36. 4-o-Fluorobenzyloxy-3-methyl-3H-imidazo(4,5-c)pyridine of m.p. 142°–144°.
37. 4-m-Fluorobenzyloxy-3-methyl-3H-imidazo(4,5-c)pyridine.
38. 4-p-Fluorobenzyloxy-3-methyl-3H-imidazo(4,5-c)pyridine.

39. 4-o-Chlorobenzyloxy-3-methyl-3H-imidazo(4,5-c)pyridine of m.p. 125°–127°.
40. 4-m-Chlorobenzyloxy-3-methyl-3H-imidazo(4,5-c)pyridine.
41. 4-p-Chlorobenzyloxy-3-methyl-3H-imidazo(4,5-c)pyridine of m.p. 145°–147°
42. 3-Methyl-4-o-nitrobenzyloxy-3H-imidazo(4,5-c)pyridine.
43. 3-Methyl-4-m-nitrobenzyloxy-3H-imidazo(4,5-c)pyridine.
44. 3-Methyl-4-p-nitrobenzyloxy-3H-imidazo(4,5-c)pyridine.
45. 3-Methyl-4-o-trifluoromethylbenzyloxy-3H-imidazo(4,5-c)pyridine.
46. 3-Methyl-4-m-trifluoromethylbenzyloxy-3H-imidazo(4,5-c)pyridine.
47. 3-Methyl-4-p-trifluoromethylbenzyloxy-3H-imidazo(4,5-c)pyridine.
48. 4-(2,3-Dichlorobenzyloxy)-3-methyl-3H-imidazo(4,5-c)pyridine.
49. 4-(2,4-Dichlorobenzyloxy)-3-methyl-3H-imidazo(4,5-c)pyridine of m.p. 139°–140°.
50. 4-(2,5-Dichlorobenzyloxy)-3-methyl-3H-imidazo(4,5-c)pyridine.
51. 4-(2,6-Dichlorobenzyloxy)-3-methyl-3H-imidazo(4,5-c)pyridine.
52. 4-(3,4-Dichlorobenzyloxy)-3-methyl-3H-imidazo(4,5-c)pyridine.
53. 4-(3,5-Dichlorobenzyloxy)-3-methyl-3H-imidazo(4,5-c)pyridine.
54. 4-(2,4-Dinitrobenzyloxy)-3-methyl-3H-imidazo(4,5-c)pyridine.
55. 4-(3,4-Dinitrobenzyloxy)-3-methyl-3H-imidazo(4,5-c)pyridine.
56. 4-(3,5-Dinitrobenzyloxy)-3-methyl-3H-imidazo(4,5-c)pyridine.
57. 4-(2-Chloro-6-fluorobenzyloxy)-3-methyl-3H-imidazo(4,5-c)-pyridine.
58. 4-(2-Chloro-4-nitrobenzyloxy)-3-methyl-3H-imidazo(4,5-c)pyridine.
59. 4-(2-Chloro-5-nitrobenzyloxy)-3-methyl-3H-imidazo(4,5-c)pyridine.
60. 4-(4-Chloro-2-nitrobenzyloxy)-3-methyl-3H-imidazo(4,5-c)pyridine.
61. 4-(4-Chloro-3-nitrobenzyloxy)-3-methyl-3H-imidazo(4,5-c)pyridine.
62. 4-(5-Chloro-2-nitrobenzyloxy)-3-methyl-3H-imidazo(4,5-c)pyridine.

EXAMPLE 63

2.76 g of Na is dissolved in 180 ml of ethanol; 19.1 g of o-chlorobenzylmercaptan and 16.76 g of 4-chloro-1-methyl-1H-imidazo(4,5-c)pyridine are added; the mixture is boiled for 16 hours and evaporated; and the residue is worked up in the customary manner to give 4-o-chloro-benzylthio-1-methyl-1H-imidazo(4,5-c)pyridine of m.p. 152°–155° (from ethanol).

EXAMPLES 64 TO 126

The following compounds are obtained analogously to Example 63 from the corresponding 4-chloro-imidazo(4,5-c)pyridines with the corresponding mercaptans:
64. 4-(1-Benzothienyl-3-methylthio)-1-methyl-1H-imidazo(4,5-c)pyridine of m.p. 146°–148°.
65. 4-(1-Benzothienyl-3-methylthio)-1-butyl-1H-imidazo(4,5-c)pyridine of m.p. 157°–159°.
66. 4-(1-Benzothienyl-3-methylthio)-1-cyclopropylmethyl-1H-imidazo(4,5-c)pyridine of m.p. 103°–104°.
67. 4-(1-Benzothienyl-2-methylthio)-1-methyl-1H-imidazo(4,5-c)pyridine of m.p. 152°–154°.
68. 4-(Naphthyl-1-methylthio)-1-methyl-1H-imidazo(4,5-c)pyridine of m.p. 143°–144°.
69. 4-(Naphthyl-2-methylthio)-1-methyl-1H-imidazo(4,5-c)pyridine of m.p. 156°–158°.
70. 4-o-Fluorobenzylthio-1-methyl-1H-imidazo(4,5-c)pyridine.
71. 4-m-Fluorobenzylthio-1-methyl-1H-imidazo(4,5-c)pyridine.
72. 4-p-Fluorobenzylthio-1-methyl-1H-imidazo(4,5-c)pyridine.
73. 4-m-Chlorobenzylthio-1-methyl-1H-imidazo(4,5-c)pyridine.
74. 4-p-Chlorobenzylthio-1-methyl-1H-imidazo(4,5-c)pyridine of m.p. 151°–153°.
75. 1-Methyl-4-o-nitrobenzylthio-1H-imidazo(4,5-c)pyridine.
76. 1-Methyl-4-m-nitrobenzylthio-1H-imidazo(4,5-c)pyridine.
77. 1-Methyl-4-p-nitrobenzylthio-1H-imidazo(4,5-c)pyridine.
78. 1-Methyl-4-o-trifluoromethylbenzylthio-1H-imidazo(4,5-c)pyridine.
79. 1-Methyl-4-m-trifluoromethylbenzylthio-1H-imidazo(4,5-c)pyridine.
80. 1-Methyl-4-p-trifluoromethylbenzylthio-1H-imidazo(4,5-c)pyridine.
81. 4-(2,3-Dichlorobenzylthio)-1-methyl-1H-imidazo(4,5-c)pyridine.
82. 4-(2,4-Dichlorobenzylthio)-1-methyl-1H-imidazo(4,5-c)pyridine of m.p. 126°–128°
83. 4-(2,5-Dichlorobenzylthio)-1-methyl-1H-imidazo(4,5-c)pyridine.
84. 4-(2,6-Dichlorobenzylthio)-1-methyl-1H-imidazo(4,5-c)pyridine.
85. 4-(3,4-Dichlorobenzylthio)-1-methyl-1H-imidazo(4,5-c)pyridine.
86. 4-(3,5-Dichlorobenzylthio)-1-methyl-1H-imidazo(4,5-c)pyridine.
87. 4-(2,4-Dinitrobenzylthio)-1-methyl-1H-imidazo(4,5-c)pyridine.
88. 4-(3,4-Dinitrobenzylthio)-1-methyl-1H-imidazo(4,5-c)pyridine.
89. 4-(3,5-Dinitrobenzylthio)-1-methyl-1H-imidazo(4,5-c)pyridine.
90. 4-(2-Chloro-6-fluorobenzylthio)-1-methyl-1H-imidazo(4,5-c)pyridine.
91. 4-(2-Chloro-4-nitrobenzylthio)-1-methyl-1H-imidazo(4,5-c)pyridine.
92. 4-(2-Chloro-5-nitrobenzylthio)-1-methyl-1H-imidazo(4,5-c)pyridine.
94. 4-(4-Chloro-2-nitrobenzylthio)-1-methyl-1H-imidazo(4,5-c)pyridine.
94. 4-(4-Chloro-3-nitrobenzylthio)-1-methyl-1H-imidazo(4,5-c)pyridine.
95. 4-(5-Chloro-2-nitrobenzylthio)-1-methyl-1H-imidazo(4,5-c)pyridine.
96. 4-(1-Benzothienyl-3-methylthio)-3-methyl-3H-imidazo(4,5-c)pyridine of m.p. 144°–147°; hemimalonate, m.p. 139°–140°; hemimaleate, m.p. 135°–137°.
97. 4-(1-Benzothienyl-2-methylthio)-3-methyl-3H-imidazo(4,5-c)pyridine.
98. 4-(Naphthyl-1-methylthio)-3-methyl-3H-imidazo(4,5-c)pyridine of m.p. 159°–160°.

99. 4-(Naphthyl-2-methylthio)-3-methyl-3H-imidazo(4,5-c)pyridine of m.p. 119°–120°.
100. 4-o-Fluorobenzylthio-3-methyl-3H-imidazo(4,5-c)pyridine of m.p. 93°–94°.
101. 4-m-Fluorobenzylthio-3-methyl-3H-imidazo(4,5-c)pyridine.
102. 4-p-Fluorobenzylthio-3-methyl-3H-imidazo(4,5-c)pyridine.
103. 4-o-Chlorobenzylthio-3-methyl-3H-imidazo(4,5-c)pyridine of m.p. 119°–120°.
104. 4-m-Chlorobenzylthio-3-methyl-3H-imidazo(4,5-c)pyridine.
105. 4-p-Chlorobenzylthio-3-methyl-3H-imidazo(4,5-c)pyridine of m.p. 118°–119°.
106. 3-Methyl-4-o-nitrobenzylthio-3H-imidazo(4,5-c)pyridine.
107. 3-Methyl-4-m-nitrobenzylthio-3H-imidazo(4,5-c)pyridine.
108. 3-Methyl-4-p-nitrobenzylthio-3H-imidazo(4,5-c)pyridine.
109. 3-Methyl-4-o-trifluoromethylbenzylthio-3H-imidazo(4,5-c)pyridine of m.p. 126°–128°.
110. 3-Methyl-4-m-trifluoromethylbenzylthio-3H-imidazo(4,5-c)pyridine.
111. 3-Methyl-4-p-trifluoromethylbenzylthio-3H-imidazo(4,5-c)pyridine.
112. 4-(2,3-Dichlorobenzylthio)-3-methyl-3H-imidazo(4,5-c)pyridine.
113. 4-(2,4-Dichlorobenzylthio)-3-methyl-3H-imidazo(4,5-c)pyridine of m.p. 101°–102°.
114. 4-(2,5-Dichlorobenzylthio)-3-methyl-3H-imidazo(4,5-c)pyridine.
115. 4-(2,6-Dichlorobenzylthio)-3-methyl-3H-imidazo(4,5-c)pyridine of m.p. 148°–150°.
116. 4-(3,4-Dichlorobenzylthio)-3-methyl-3H-imidazo(4,5-c)pyridine.
117. 4-(3,5-Dichlorobenzylthio)-3-methyl-3H-imidazo(4,5-c)pyridine.
118. 4-(2,4-Dinitrobenzylthio)-3-methyl-3H-imidazo(4,5-c)pyridine.
119. 4-(3,4-Dinitrobenzylthio)-3-methyl-3H-imidazo(4,5-c)pyridine.
120. 4-(3,5-Dinitrobenzylthio)-3-methyl-3H-imidazo(4,5-c)pyridine.
121. 4-(2-Chloro-6-fluorobenzylthio)-3-methyl-3H-imidazo(4,5-c)pyridine of m.p. 137°–139°.
122. 4-(2-Chloro-4-nitrobenzylthio)-3-methyl-3H-imidazo(4,5-c)pyridine.
123. 4-(2-Chloro-5-nitrobenzylthio)-3-methyl-3H-imidazo(4,5-c)pyridine.
124. 4-(4-Chloro-2-nitrobenzylthio)-3-methyl-3H-imidazo(4,5-c)pyridine.
125. 4-(4-Chloro-3-nitrobenzylthio)-3-methyl-3H-imidazo(4,5-c)pyridine.
126. 4-(5-Chloro-2-nitrobenzylthio)-3-methyl-3H-imidazo(4,5-c)pyridine.

EXAMPLE 127

A solution of 16.76 g of 4-chloro-1-methyl-1H-imidazo(4,5-c)pyridine and 35 g of o-chlorobenzylamine in 500 ml of xylene is boiled for 24 hours. On cooling, 4-o-chlorobenzylamino-1-methyl-1H-imidazo(4,5-c)pyridine of m.p. 173°–176° crystallizes out.

EXAMPLE 128

A mixture of 16.76 g of 4-chloro-3-methyl-3H-imidazo(4,5-c)pyridine and 30 g of o-fluorobenzylamine is melted at 180° for 2 hours. After customary working up, 4-o-fluorobenzylamino-3-methyl-3H-imidazo-(4,5-c)pyridine of m.p. 163°–164° is obtained.

EXAMPLES 129 TO 188

The following compounds are obtained analogously to Example 127 from the corresponding 4-chloro-imidazo(4,5-c)pyridines and the corresponding amines:
129. 4-(1-Benzothienyl-3-methylamino)-1-methyl-1H-imidazo(4,5-c)pyridine of m.p. 120°–125°. Hydrochloride, m.p. 308°–310°.
130. 4-(1-Benzothienyl-2-methylamino)-1-methyl-1H-imidazo(4,5-c)pyridine of m.p. 160°–162°.
131. 4-(Naphthyl-1-methylamino)-1-methyl-1H-imidazo(4,5-c)pyridine of m.p. 152°–154°; hydrochloride, m.p. 317°–318°.
132. 4-(Naphthyl-2-methylamino)-1-methyl-1H-imidazo(4,5-c)pyridine.
133. 4-o-Fluorobenzylamino-1-methyl-1H-imidazo(4,5-c)pyridine.
134. 4-m-Fluorobenzylamino-1-methyl-1H-imidazo(4,5-c)pyridine.
135. 4-p-Fluorobenzylamino-1-methyl-1H-imidazo(4,5-c)pyridine.
136. 4-m-Chlorobenzylamino-1-methyl-1H-imidazo(4,5-c)pyridine.
137. 4-p-Chlorobenzylamino-1-methyl-1H-imidazo(4,5-c)pyridine.
138. 1-Methyl-4-o-nitrobenzylamino-1H-imidazo(4,5-c)pyridine.
139. 1-Methyl-4-m-nitrobenzylamino-1H-imidazo(4,5-c)pyridine.
140. 1-Methyl-4-p-nitrobenzylamino-1H-imidazo(4,5-c)pyridine.
141. 1-Methyl-4-o-trifluoromethylbenzylamino-1H-imidazo(4,5-c)pyridine.
142. 1-Methyl-4-m-trifluoromethylbenzylamino-1H-imidazo(4,5-c)pyridine.
143. 1-Methyl-4-p-trifluoromethylbenzylamino-1H-imidazo(4,5-c)pyridine.
144. 4-(2,3-Dichlorobenzylamino)-1-methyl-1H-imidazo(4,5-c)pyridine.
145. 4-(2,4-Dichlorobenzylamino)-1-methyl-1H-imidazo(4,5-c)pyridine of m.p. 150°–153°.
146. 4-(2,3-Dichlorobenzylamino)-1-methyl-1H-imidazo(4,5-c)pyridine.
147. 4-(2,6-Dichlorobenzylamino)-1-methyl-1H-imidazo(4,5-c)pyridine.
148. 4-(3,4-Dichlorobenzylamino)-1-methyl-1H-imidazo(4,5-c)pyridine.
149. 4-(3,5-Dichlorobenzylamino)-1-methyl-1H-imidazo(4,5-c)pyridine.
150. 4-(2,4-Dinitrobenzylamino)-1-methyl-1H-imidazo(4,5-c)pyridine.
151. 4-(3,4-Dinitrobenzylamino)-1-methyl-1H-imidazo(4,5-c)pyridine.
152. 4-(3,5-Dinitrobenzylamino)-1-methyl-1H-imidazo(4,5-c)pyridine.
153. 4-(2-Chloro-6-fluorobenzylamino)-1-methyl-1H-imidazo(4,5-c)pyridine.
154. 4-(2-Chloro-4-nitrobenzylamino)-1-methyl-1H-imidazo(4,5-c)pyridine.
155. 4-(2-Chloro-5-nitrobenzylamino)-1-methyl-1H-imidazo(4,5-c)pyridine.
156. 4-(4-Chloro-2-nitrobenzylamino)-1-methyl-1H-imidazo(4,5-c)pyridine.
157. 4-(4-Chloro-3-nitrobenzylamino)-1-methyl-1H-imidazo(4,5-c)pyridine.

158. 4-(5-Chloro-2-nitrobenzylamino)-1-methyl-1H-imidazo(4,5-c)pyridine.
159. 4-(1-Benzothienyl)-3-methylamino)-3-methyl-3H-imidazo(4,5-c)pyridine of m.p. 162°–164°.
160. 4-(1-Benzothienyl-2-methylamino)-3-methyl-3H-imidazo(4,5-c)pyridine.
161. 4-(Naphthyl-1-methylamino)-3-methyl-3H-imidazo(4,5-c)pyridine.
162. 4-(Naphthyl-2-methylamino)-3-methyl-3H-imidazo(4,5-c)pyridine.
163. 4-m-Fluorobenzylamino-3-methyl-3H-imidazo(4,5-c)pyridine.
164. 4-p-Fluorobenzylamino-3-methyl-3H-imidazo(4,5-c)pyridine.
165. 4-o-Chlorobenzylamino-3-methyl-3H-imidazo(4,5-c)pyridine of m.p. 179°–180°.
166. 4-m-Chlorobenzylamino-3-methyl-3H-imidazo(4,5-c)pyridine.
167. 4-p-Chlorobenzylamino-3-methyl-3H-imidazo(4,5-c)pyridine.
168. 3-Methyl-4-o-nitrobenzylamino-3H-imidazo(4,5-c)pyridine.
169. 3-Methyl-4-m-nitrobenzylamino-3H-imidazo(4,5-c)pyridine.
170. 3-Methyl-4-p-nitrobenzylamino-3H-imidazo(4,5-c)pyridine.
171. 3-Methyl-4-o-trifluoromethylbenzylamino-3H-imidazo(4,5-c)pyridine.
172. 3-Methyl-4-m-trifluoromethylbenzylamino-3H-imidazo(4,5-c)pyridine.
173. 3-Methyl-4-p-trifluoromethylbenzylamino-3H-imidazo(4,5-c)pyridine.
174. 4-(2,3-Dichlorobenzylamino)-3-methyl-3H-imidazo(4,5-c)pyridine. 175. 4-(2,4-Dichlorobenzylamino)-3-methyl-3H-imidazo(4,5-c)pyridine of m.p. 178°–179°.
176. 4-(2,4-Dichlorobenzylamino)-3-methyl-3H-imidazo(4,5-c)pyridine.
177. 4-(2,6-Dichlorobenzylamino)-3-methyl-3H-imidazo(4,5-c)pyridine of m.p. 181°–185°.
178. 4-(3,4-Dichlorobenzylamino)-3-methyl-3H-imidazo(4,5-c)pyridine.
179. 4-(3,5-Dichlorobenzylamino)-3-methyl-3H-imidazo(4,5-c)pyridine.
180. 4-(2,4-Dinitrobenzylamino)-3-methyl-3H-imidazo(4,5-c)pyridine.
181. 4-(3,4-Dinitrobenzylamino)3-methyl-3H-imidazo(4,5-c)pyridine.
182. 4-(3,5-Dinitrobenzylamino)-3-methyl-3H-imidazo(4,5-c)pyridine.
183. 4-(2-Chloro-6-fluorobenzylamino)-3-methyl-3H-imidazo(4,5-c)pyridine.
184. 4-(2-Chloro-4-nitrobenzylamino)-3-methyl-3H-imidazo(4,5-c)pyridine.
185. 4-(2-Chloro-5-nitrobenzylamino)-3-methyl-3H-imidazo(4,5-c)pyridine.
186. 4-(4-Chloro-2-nitrobenzylamino)-3-methyl-3H-imidazo(4,5-c)pyridine.
187. 4-(4-Chloro-3-nitrobenzylamino)-3-methyl-3H-imidazo(4,5-c)pyridine.
188. 4-(5-Chloro-2-nitrobenzylamino)-3-methyl-3H-imidazo(4,5-c)pyridine.

EXAMPLE 189

A mixture of 17.9 of 1-methyl-4-methylthio-1H-imidazo(4,5-c)pyridine (m.p. 170°–175°) and 28 g of o-chlorobenzylamine is heated to 170°–180° for 20 hours. After cooling and customary working up, 4-o-chlorobenzylamino-1-methyl-1H-imidazo(4,5-c)pyridine of m.p. 173°–176° is obtained.

EXAMPLE 190

A mixture of 2.81 g of 4-(1-benzothienyl-3-methoxy)-1H-imidazo(4,5-c)pyridine (obtainable from 1-benzothienyl-3-methanol and 4-chloro-1H-imidazo(4,5-c)pyridine), 1.7 g of methyl iodide, 1.7 g of potassium carbonate and 50 ml of acetone is stirred at 20° for two days. The mixture is filtered, the filtrate is evaporated and the residue is working up in the customary manner to give 4-(1-benzothienyl-3-methoxy)-1-methyl-1H-imidazo(4,5-c)pyridine of m.p. 200°–204°.

EXAMPLES 191 to 377

The compounds described in Examples 2 to 188 are obtained and analogously to Example 190 from the corresponding imidazopyridines which are unsubstituted in the 1- and 3-position, by alkylation.

EXAMPLE 378

A mixture of 2.85 g of 3-amino-2-(1-benzothienyl-3-methoxy)-4-methylamino-pyridine (obtainable from 3-amino-2-chloro-4-methylamino-pyridine and 1-benzothienyl-3-methanol) and 0.27 g of s-triazine is kept at 210° for one minute and is cooled. The crystallization from ethyl acetate/tetrahydrofuran gives 4-(1-benzothienyl-3-methoxy)-1-methyl-1H-imidazo(4,5-c)pyridine of m. p. 200°–204°.

EXAMPLES 379 to 565

The compounds described in Examples 2 to 188 are obtained analogously to Example 378 from the corresponding compounds of the Formula VI with s-triazine.

EXAMPLE 566

A mixture of 28.5 g of 3-amino-2-(1-benzothienyl-3-methoxy)-4-methylamino-pyridine, 100 ml of triethyl orthoformate and 40 ml of acetic anhydride is heated to 100° for 30 minutes. After evaporation and customary working up, 4-(1-benzothienyl-3-methoxy)-1-methyl-1H-imidazo(4,5-c)pyridine of m.p. 200°–204° is obtained.

EXAMPLES 567 to 753

The compounds described in Examples 2 to 188 are obtained analogously to Example 566 from the corresponding compounds of the general Formula VI with triethyl orthoformate.

EXAMPLES 754 to 762

In analogy to Example 1 there are obtained:
754. 4-(1-Benzothienyl-3-methoxy)-1-ethyl-1H-imidazo(4,5-c)pyridine of m.p. 101°–104°.
755. 4-(1-Benzothienyl-3-methoxy)-1-propyl-1H-imidazo(4,5-c)pyridine, hemifumarate, m.p. 106°–110°.
756. 4-o-Chlorobenzyloxy-1-ethyl-1H-imidazo(4,5-c)pyridine of m.p. 97°–99°.
757. 4-(2,4-Dichlorobenzyloxy)-1-ethyl-1H-imidazo(4,5-c)pyridine of m.p. 112°–114°.
758. 4-(1-Benzothienyl-3-methoxy)-3-ethyl-3H-imidazo(4,5-c)pyridine of m.p. 116°–118°.
759. 4-(1-Benzothienyl-3-methoxy)-3-propyl-3H-imidazo(4,5-c)pyridine of m.p. 95°–97°.
760. 4-(1-Benzothienyl-3-methoxy)-3-butyl-3H-imidazo(4,5-c)pyridine of m.p. 88°–89°.

761.  4-(2,4-Dichlorobenzyloxy)-3-ethyl-3H-imidazo(4,5c)pyridine of m.p. 105°-107°.
762.  4-(2,4-Dichlorobenzyloxy)-3-propyl-3H-imidazo(4,5-c)pyridine of m.p. 107°-109°.

EXAMPLES 763 to 774

In analogy to Example 63 there are obtained:
763.  4-(1-Benzothienyl-3-methylthio)-1-ethyl-1H-imidazo(4,5-c)pyridine of m.p. 127°-129°.
764.  4-(1-Benzothienyl-3-methylthio)-1-propyl-1H-imidazo(4,5-c)pyridine of m.p. 118°-121°.
765.  4-o-Chlorobenzylthio-1-ethyl-1H-imidazo(4,5-c)pyridine of m.p. 103°-106°.
766.  4-o-Chlorobenzylthio-1-propyl-1H-imidazo(4,5-c)pyridine of m.p. 72°-76°.
767.  4-(2,4-Dichlorobenzylthio)-1-ethyl-1H-imidazo(4,5-c)pyridine of m.p. 152°-154°.
768.  4-(2,4-Dichlorobenzylthio)-1-propyl-1H-imidazo(4,5-c)pyridine of m.p. 126°-128°.
769.  4-(1-Benzothienyl-3-methylthio)-3-ethyl-3H-imidazo(4,5-c)pyridine of m.p. 87°-89°.
779.  4-(1-Benzothienyl-3-methylthio)-3-propyl-3H-imidazo(4,5-c)pyridine of m.p. 85°-87°.
771.  4-(1-Benzothienyl-3-methylthio)-3-butyl-3H-imidazo(4,5-c)pyridine, hemifumarate, m.p. 110°-112°.
772.  4-(1-Benzothienyl-3-methylthio)-3-cyclopropylmethyl-3H-imidazo(4,5-c)pyridine of m.p. 135°-136°.
773.  4-o-Chlorobenzylthio-3-ethyl-3H-imidazo(4,5-c)pyridine, hemifumarate, m.p. 126°-130°.
774.  4-o-Chlorobenzylthio-3-propyl-3H-imidazo(4,5-c)pyridine, dihydrochloride, m.p. 125°-132°.

EXAMPLE 775

A mixture of 7.5 g of 4-chloro-1-methyl-1H-imidazo(4,5-c)pyridine, 7.1 g of 2-chlorobenzyl alcohol, 3.3 g of KOH and 100 ml of acetonitrile is refluxed for 7 hours. The solvent is removed and the residue is worked up in the customary manner (water/methylene chloride) to give 4-o-Chlorobenzyloxy-1-methyl-1H-imidazo(4,5-c)pyridine, m.p. 132°-135°.

The examples which follow relate to pharmaceutical formulations which contain compounds of Formula I or their acid addition salts:

EXAMPLE A: TABLETS

A mixture of 1 kg of 4-(1-benzothienyl-3-methoxy)-3-methyl-3H-imidazo(4,5-c)pyridine ("B"), 4 kg of lactose, 1.2 kg of potato starch, 0.2 kg of talc and 0.1 kg of magnesium stearate is pressed into tablets in the customary manner, such that each tablet contains 100 mg of active compound.

EXAMPLES B: DRAGEES

Tablets are pressed analogously to Example A, and are then covered with a coating of sucrose, potato starch, talc, tragacanth and colorant in the customary manner.

EXAMPLE C: CAPSULES 10 kg of "B" is filled into hard gelatine capsules in the customary manner such that each capsule contains 50 mg of active compound.

EXAMPLE D: AMPOULES

A solution of 1 kg of "B" hydrochloride in 100 l of doubly distilled water is sterile-filtered, filled into ampoules and lyophilized under sterile conditions and the ampoules are closed under sterile conditions. Each ampoule contains 50 mg of active compound.

Tablets, dragees, capsules and ampoules containing one or more of the other active compounds of the Formula I and/or their physiologically acceptable acid addition salts can be obtained analogously.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

For the determination of direct GABA-agonistic activity, the test of D. R. Curtis et al. (l.c.) was adapted to mice. Intraperitoneal injection of 100 mg/kg of
4-(1-benzothienyl-3-methoxy)-3-methyl-3H-imidazo(4,5-c)pyridine (Example 2),
4-(1-benzothienyl-2-methoxy)-1-methyl-1H-imidazo(4,5-c)pyridine (Example 3),
4-p-chlorobenzyloxy-1-methyl-1H-imidazo(4,5-c)pyridine (Example 11), or
4-(2,4-dichlorobenzyloxy)-1-methyl-1H-imidazo(4,5-c)-pyridine (Example 19), respectively, in each case, inhibited the convulsive action of 0.5 mg/kg of biculline.

The benzodiazepine antagonistic activity of 4-o-chlorobenzylthio-1-methyl-1H-imidazo(4,5-c)pyridine (Example 63), or
4-(1-benzothienyl-3-methylthio)-3-methyl-3H-imidazo(4,5-c)pyridine (Example 96)
was tested in two rodent models of behavior known to have predictive value in evaluating anxiolytic activity:
(1) In the "thirsty rat model" (method cf. J. Vogel et al., Psychopharmacology vol. 21. (1971)1), 20 mg/kg intraperitoneally given of the two compounds each completely antagonized the effects of 8 mg/kg of chloridazepoxide;
(2) In a mouse model of exploratory behavior (method cf. J. N. Crawley and F. K. Goodwin, Pharmacol. Biochem. Behav. 13 (1980) 67; J. N. Carwley, ibid., 15 (1981) 695), intraperitoneal administration of 30 mg/kg of the two compounds each inhibited the behavioral changes elicated by 2 mg/kg of diazepam.

What is claimed is:
1. An imidazo(4,5-c)pyridine of the formula

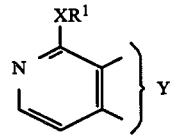

wherein
X is O, S or NH;
Y is —NR²—CH═N— or —N═CH—NR²—;
R¹ is 1-benzothienylmethyl, naphthylmethyl, or benzyl which is mono- or di-substituted by F, Cl, NO₂, CF₃ or a combination thereof, and;
R² is alkyl of 1-4 C atoms or cyclopropylmethyl,
or a physiologically acceptable acid addition salt thereof.

2. 4-(1-Benzothienyl-3-methoxy)-3-methyl-3H-imidazo(4,5-c)pyridine, a compound of claim 1.

3. A compound of claim 1 wherein Y is —N=CH—NR²—.

4. A compound of claim 1 wherein Y is —NR²—CH=N—.

5. A compound of claim 1 wherein X is O or S.

6. A compound of claim 1 wherein R¹ is 1-benzothienyl-3-methyl, o-, m- or p-fluorobenzyl, o-, m- or p-chlorobenzyl, o-, m- or p-nitrobenzyl, o-, m- or p-trifluoromethylbenzyl, or 2,3-, 2,4-, 2,5-, 2,6-, 3,4- or 3,5-dichlorobenzyl.

7. A compound of claim 1 wherein R² is methyl, ethyl or cyclopropylmethyl.

8. A compound of claim 4 wherein X is O or S.

9. A compound of claim 8 wherein R¹ is 1-benzothienyl-3-methyl, o-, m- or p-fluorobenzyl, o-, m- or p-chlorobenzyl, o-, m- or p-nitrobenzyl, o-, m- or p-trifluoromethylbenzyl, or 2,3-, 2,4-, 2,5-, 2,6-, 3,4- or 3,5-dichlorobenzyl.

10. A compound of claim 9 wherein R² is methyl, ethyl or cyclopropylmethyl.

11. A compound of the formula

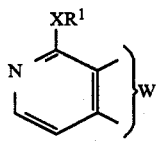

wherein
W is —NH—CH=N— or —N=CH—NH—,
X is O, S or NH, and
R¹ is 1-benzothienylmethyl, naphthylmethyl, or benzyl which is mono- or di-substituted by F, Cl, NO₂, CF₃ or a combination thereof.

12. A method of treating a patient suffering from an illness which is treatable by a GABA-agonist, comprising administering to the patient a compound of claim 1.

13. A method of claim 12 wherein the illness is cerebral infarction, epilepsy, delayed dyskinesia, Huntington's chorea, abstinence syndrome in alcoholics, alcohol withdrawal spasms, spastic conditions, anxiety, sleep disorders or pain.

14. A method of antagonizing the sedating, muscle-relaxing, atactic, hypotensive and respiration-depressive properties of tranquilizing benzodiazepines, in a patient to whom a benzodiazepine has been administered and in whom such antagonization is desired, comprising administering to the patient a compound of claim 1.

15. A method of antagonizing the sedative effect in a patient of a sedation causing medicament which has been administered to the patient, comprising administering a compound of claim 1 to the patient.

16. A method of antagonizing the effect in a patient of a medicament which attacks the benzodiazepine receptors in the patient and which has been administered to the patient, comprising administering to the patient a compound of claim 1.

17. A method of claim 14 wherein the amount of benzodiazepine administered to the patient was an overdose.

18. A pharmaceutical composition comprising an active compound of claim 1 and a pharmaceutically acceptable carrier.

19. A pharmaceutical composition of claim 18 wherein the amount of said active compound is 1–500 mg.

20. 4-o-Chlorobenzyloxy-1-methyl-1H-imidazo(4,5-c)pyridine, a compound of claim 1.

21. A method of achieving an anticonvulsive effect in a subject in need thereof comprising administering a compound of claim 1.

22. A method of achieving an anticonvulsive effect in a subject in need thereof comprising administering a compound of claim 20.

23. 4-(1-Benzothienyl-3-methylthio)-3-methyl-3H-imidazo-(4,5-c)pyridine.

* * * * *